United States Patent
Stein et al.

[11] Patent Number: 6,027,625
[45] Date of Patent: Feb. 22, 2000

[54] MINIATURIZED DISPOSABLE GELS FOR DNA ANALYSIS

[75] Inventors: Arnold Stein; Minou Bina; Weldon Vaughn, all of West Lafayette, Ind.

[73] Assignee: Purdue Research Foundation, West Lafayette, Ind.

[21] Appl. No.: 09/014,226

[22] Filed: Jan. 27, 1998

Related U.S. Application Data

[62] Division of application No. 08/769,949, Dec. 19, 1996, Pat. No. 5,759,375.
[60] Provisional application No. 60/017,437, May 17, 1996.

[51] Int. Cl.[7] .......................... G01N 27/26; G01N 27/447
[52] U.S. Cl. .......................... 204/466; 204/456; 204/605; 204/616
[58] Field of Search ........................ 204/606, 607, 204/608, 609, 610, 612, 613, 614, 615, 616, 617, 618, 619, 620, 621, 456, 457, 458, 459, 461, 462, 463, 464, 465; 435/309.1; 436/162

[56] References Cited

U.S. PATENT DOCUMENTS

| | | | |
|---|---|---|---|
| 3,616,387 | 10/1971 | Siebert et al. | 204/466 |
| 3,622,484 | 11/1971 | Cawley | 204/466 |
| 3,839,183 | 10/1974 | Klein et al. | 204/606 |
| 4,339,327 | 7/1982 | Tyler . | |
| 4,883,577 | 11/1989 | Sugimoto et al. | 204/619 |
| 5,137,613 | 8/1992 | Brumley, Jr. et al. . | |
| 5,164,065 | 11/1992 | Bettencourt et al. . | |
| 5,209,831 | 5/1993 | MacConnell . | |
| 5,217,591 | 6/1993 | Gombocz et al. . | |
| 5,228,970 | 7/1993 | Foley . | |
| 5,232,573 | 8/1993 | Rosenvold . | |
| 5,281,322 | 1/1994 | Antoinette et al. . | |
| 5,304,292 | 4/1994 | Jacobs et al. . | |
| 5,318,682 | 6/1994 | Singer . | |
| 5,370,782 | 12/1994 | Mochizuki . | |
| 5,407,552 | 4/1995 | Lebacq . | |
| 5,411,657 | 5/1995 | Leka . | |
| 5,599,434 | 2/1997 | Izmailov et al. . | |
| 5,627,022 | 5/1997 | Renfrew et al. . | |

FOREIGN PATENT DOCUMENTS

| | | | |
|---|---|---|---|
| 4-42050 | 6/1990 | Japan . | |
| 4-42050 | 2/1992 | Japan | 204/616 |
| WO 93/00986 | 1/1993 | WIPO . | |

OTHER PUBLICATIONS

Henrik Garoff and Wilhelm Ansorge, Improvements of DNA Sequencing Gels, Analytical Biochemistry, vol. 115, pp. 450–457, No Month Available 1981.

Adam T. Woolley and Richard A. Mathies, Ultra–High–Speed DNA Sequencing Using Capillart Electrophoresis Chips, Anal. Chem, vol. 67, pp. 3676–3680, Oct. 15, 1995.

Advertisement by Stratagene, Breakthrough in DNA Sequencing Technology, Nature International Weekly Journal of Science, Mar. 14, 1996.

Advertisement on DNA Sequencing with the "BaseMaster" Sequencing Kit, No Month Available 1993 Pharmacia Biotechnology Products Catalog, p. 235.

Advertisement on Chemiluminescent Detection system for DNA sequencing, New England BioLabs No Month Available 1992 and No Month Available 1995 catalogs, pp. 102–103 and pp. 136–137.

*Primary Examiner*—Jill Warden
*Assistant Examiner*—John S. Starsiak, Jr.
*Attorney, Agent, or Firm*—Woodard, Emhardt, Naughton Moriarty & McNett

[57] ABSTRACT

In acordance with the teachings of the present invention, there are provided mathods, gels, and transferring devices for loading gels. The mathods and devices of the present invention involve the use of ultra-thin, miniature, disposable, slab gels for the quick, inexpensive and high resolution analysis of polynucleotide samples.

7 Claims, 12 Drawing Sheets

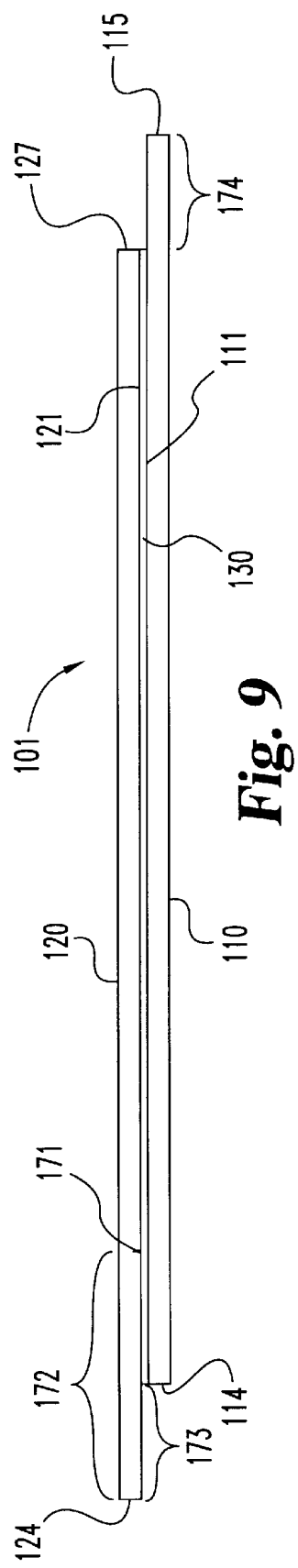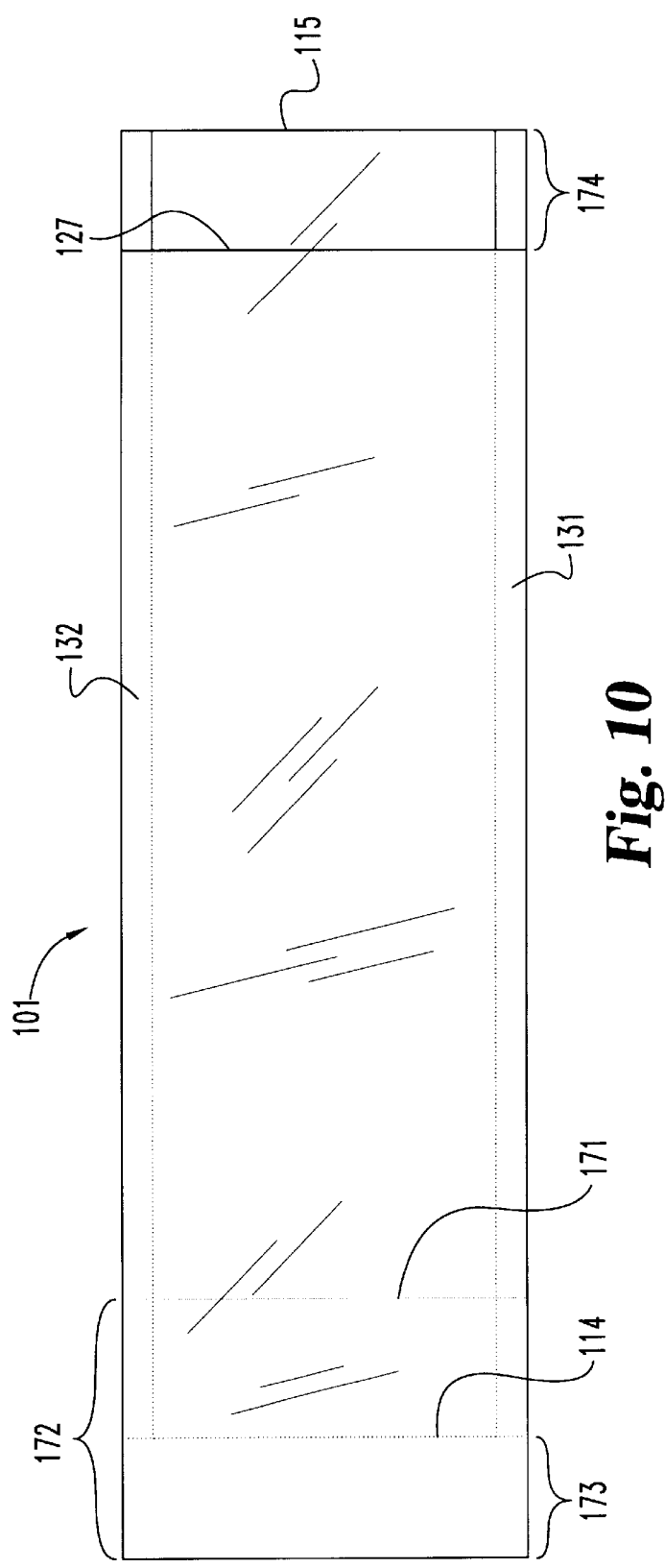

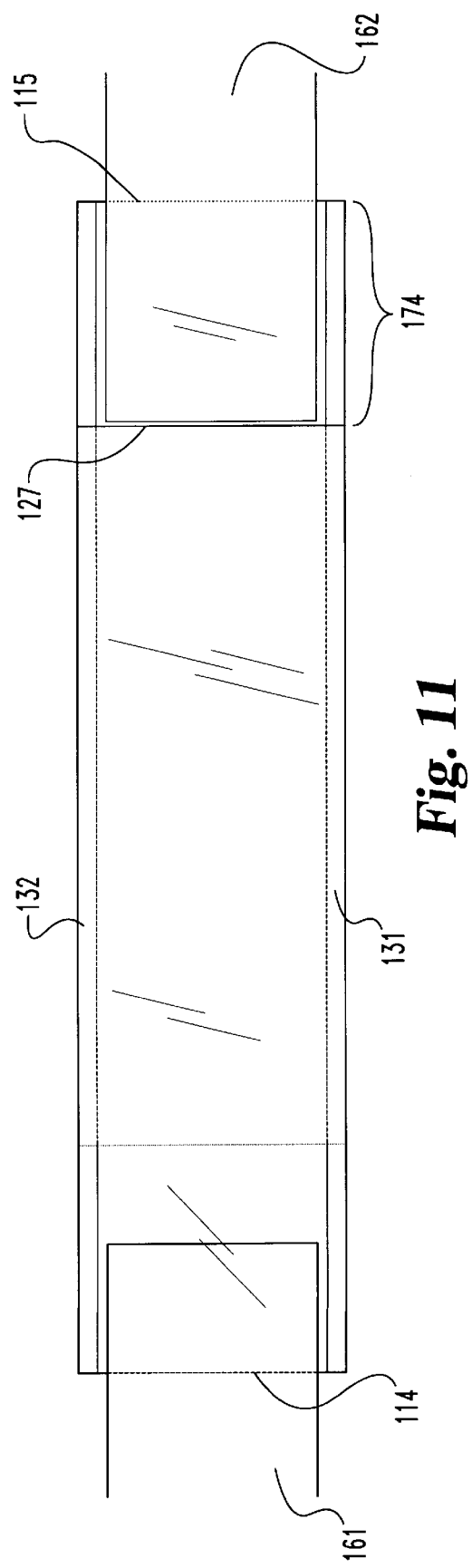

MINIATURIZED DISPOSABLE GELS FOR DNA ANALYSIS

CROSS-REFERENCES TO RELATED APPLICATIONS

This application is a division of U.S. patent application Ser. No. 08/769,949, filed Dec. 19, 1996, pending, which claims the benefit of U.S. Provisional Application No. 60/017,437, Filed May 17, 1996, now U.S. Pat. No. 5,759,375. Each of the above-named applications is incorporated by reference herein in its entirety.

STATEMENT REGARDING FEDERALLY SPONSORED RESEARCH OR DEVELOPMENT

This invention was made with government support under the following NIH grants: grant number R01 GM48341 and grant numberR01 A129121. The government has certain rights in the invention.

BACKGROUND OF THE INVENTION

1. Field of the Invention

This invention relates to electrophoresis systems and, more particularly, to novel ultra-thin, miniature, disposable, slab gel systems for speedy high resolution DNA analysis.

2. Discussion of Related Art

Electrophoresis is the resolution of a mixture of macromolecules on the basis of charge and/or size under the influence of an electric field. It is a primary analytical tool in molecular biology and biochemistry, used to separate mixtures of molecules such as proteins or nucleic acids in order to reveal their individual components. Electrophoretic analysis is based upon the fact that each molecule is characterized by a particular electrophoretic mobility under a given set of conditions. Polyacrylamide gel, agarose, cellulose or granulated gels are commonly used as stabilizing media, these gels being porous materials through which the sample components can migrate in an electric field. The electric field applied to the gel causes samples to migrate through the gel.

Deoxyribonucleic acid (DNA), for example, which is negatively charged, moves toward the positive electrode; smaller fragments of DNA migrating faster through the gel than larger fragments. DNA bands, consisting of resolved DNA chain sizes, can be detected by a number of methods. For example, isotopically labeled DNA may be detected by exposure of the gel to x-ray film.

DNA analysis can be separated into two categories: low resolution DNA analysis and high resolution DNA analysis. In low resolution analysis, double-stranded DNA fragments are run on non-denaturing polyacrylamide or agarose gels. The resolution obtained for such analysis is typically about plus or minus 10 or more nucleotide pairs. In high resolution analysis, single-stranded DNA fragments are run on denaturing polyacrylamide gels. This type of analysis separates DNA at single base resolution and is often used for DNA sequencing. The focus of the present invention is upon high resolution DNA analysis, although gel systems of the present invention are useful for either application.

It is common practice to conduct polyacrylamide gel electrophoresis in a buffered gel that was polymerized between two flat plates, usually transparent glass separated by plastic spacers. In order to provide accurate sample resolution, it is necessary that the gel thickness be uniform. It is important to avoid factors which affect electrophoretic mobility other than the characteristics of the molecules being separated. In traditional use, the gel is positioned vertically between two buffer chambers so that buffer is in contact with the gel. Samples are applied into wells formed at the top of the gel and a voltage is applied between the buffers which causes the samples to migrate within the gel. Upon completion of sample separation, the gel is separated from the plates for analysis.

Procedures for preparing and running gels for high resolution DNA analysis are presently hindered by several limitations. For instance, making and using conventional gels are technically demanding and labor intensive tasks, requiring substantial expertise. Additionally, a typical gel requires a relatively large DNA sample and must run for at least several hours to achieve adequate band separation. Further, glass plates used to make gels under current practices must be scrupulously cleaned before they can be reused.

Although the development of automated laser fluorescence systems represented a major breakthrough in large-scale DNA analysis, and some research institutions now have DNA sequencing facilities, many molecular biology laboratories still perform small-scale DNA analysis manually. For example, DNA sequencing gels, prepared in the laboratory, are often run with only a few samples loaded in order to verify or characterize a recombinant DNA construct. Also, there are other types of commonly-performed protocols, using isotope-labeled DNA, where the researcher wants to be able to quickly and easily analyze the DNA by denaturing gel electrophoresis in his or her own laboratory.

Attempts to increase the speed of electrophoretic separations have resulted in the development of capillary gel electrophoresis and ultrathin slab gels. In both of these methods, the lower electrical conductivity and greater heat dissipation than conventional gels allow much higher electric fields to be applied without damage to the gel by Joule heating. Electrophoresis times have been shortened approximately 20-fold compared with conventional methods. However, the long fused silica capillaries are expensive and difficult to work with, and ultrathin slab gels require special apparatus and techniques for pouring the gels.

Apparently, miniaturization had not been considered an option for DNA sequencing because it was generally beleived that small gels would lack the required resolution. This belief turns out to be incorrect when small volumes of sample are suitably loaded. At this time, the present inventors know of only one other miniaturized DNA sequencing system (Woolley, A. T. and Mathies, R. A., Anal. Chem. 1995, 67, 3676–3680). It was shown therein that DNA can be sequenced using gels formed in capillaries etched into small glass plates, termed capillary electrophoreseis (CE) chips. In the present invention, etched plates are not required. Each of the capillaries on a CE chip required 4 reservoirs with attached wires, two reservoirs for electrophoretic sample injection and two for sample separation. Reservoirs (60 in all) had to be sealed into the "chip" in a leak-free fashion. In the present invention, a novel, much simpler sample application system is used. Additionally, the CE chips required 1 $\mu$l of a 100-fold concentrated sample (compared to a conventional sample) per lane. The high DNA concentration used was necessary in order to detect the fluorescently labeled DNA by laser confocal microscopy. This amount of DNA loaded corresponds to about 50 times more than is used for a traditional gel. In contrast, the present invention requires only about $\frac{1}{20}$ the amount of DNA that is usually applied to a traditional gel.

The problems in the art are overcome by the present invention in which a simple inexpensive, disposable, miniaturized gel system is provided. In a preferred use, gel systems of the present invention are capable of very fast high resolution DNA analysis using extremely small samples.

SUMMARY OF THE INVENTION

Briefly describing one aspect of the present invention, there is provided an ultrathin, miniature, disposable slab gel that is suitable for quick, high resolution analysis of minute DNA samples. The term "gel," as used herein, is intended to refer to a gel medium and the structures used to form and handle the gel medium. The term "gel sandwich" is also used synonymously with "gel" herein. The term "gel medium" is intended to designate porous materials through which sample polynucleotide molecules migrate in an electric field, for example, polyacrylamide gel, agarose, cellulose and granulated gels.

A preferred embodiment of an inventive gel comprises a bottom plate having a first interior surface; a top plate overlying the bottom plate in opposing spaced apart relationship, said top plate having a second interior surface facing the first interior surface of the bottom plate; a spacing device positioned between the top plate and the bottom plate and substantially uniformly spacing the first interior surface from the second interior surface a distance of about 10.0 $\mu$m to about 50 $\mu$m; and a gel medium substantially filling a space between the first interior surface, the second interior surface, and the spacing device, the gel medium being adapted to permit migration of polynucleotides (DNA or RNA molecules) upon application of an electric field across the gel medium.

In another aspect of the present invention, there is provided a device for transferring samples to a miniature gel for electrophoresis, comprising a body having a predetermined number of teeth extending therefrom; each tooth defining a corresponding longitudinal axis; in which the distance between a proximal end and a distal end of each of the teeth is within a range of about 1.0 mm to about 2.5 mm; in which the longitudinal axes are substantially parallel to each other; in which the longitudinal axes lie substantially in a plane; in which the distal ends of all of the teeth substantially lie in a line which is substantially perpendicular to a longitudinal axis of any of the teeth; in which the teeth are closely spaced and are from about 0.010 inches to about 0.025 inches wide and from about 0.005 inches to about 0.010 inches thick; and in which the thickness of the distal end of each tooth is reduced to a sharp edge.

In accordance with another aspect of the present invention, there is provided a method for preparing an ultrathin, miniature, disposable slab gel comprising the steps of: (a) providing a sequencing gel solution in which polymerization is initiated; (b) causing a bottom plate, a top plate and a spacing device to be substantially submerged in the solution; and (c) making a gel sandwich while the plates and the spacing device are substantially submerged in the solution. A preferred embodiment of this method also comprises the additional step, after removal from the solution, of providing a substantially even inward pressure on the bottom and top plates until the gel solution is completely polymerized, thus forming a gel having a gel medium positioned therein.

Another aspect of the present invention provides a method for loading samples onto a gel comprising the steps of: (a) providing a gel wherein a loading region of a gel medium is exposed; (b) providing a device for transferring samples to the gel, comprising a body having a number of teeth extending from the body; (c) wetting one or more of the teeth with an effective amount of one or more samples; and (d) stamping the teeth of the transferring device into the loading region of the gel medium such that the teeth cut substantially through the gel medium.

In another aspect of the present invention there is provided a method for performing high resolution DNA analysis comprising the steps of (a) loading one or more samples onto a gel according to the above described method; (b) applying a predetermined electric field to the gel medium for a length of time effective to separate components of the sample in the gel medium; and (c) detecting the DNA bands.

It is an object of the present invention to provide miniature slab gels which are easy and inexpensive to make and use.

Additionally, it is an object of the present invention to provide gels and methods which are capable of performing high resolution DNA analysis more quickly than systems of the prior art.

It is also an object of the present invention to provide gels which may be readily manufactured, either wholly or in easily assembled parts, quickly and in a large quantity.

It is another object of the present invention to provide a gel which is disposable.

Finally, it is an object of the present invention to provide a gel which is capable of performing high resolution DNA analysis of extremely small samples.

Further objects, advantages and features of the present invention will be apparent from the drawings and detailed description herein.

BRIEF DESCRIPTION OF THE DRAWINGS

Although the characteristic features of this invention will be particularly pointed out in the claims, the invention itself, and the manner in which it may be made and used, may be better understood by referring to the following descriptions taken in connection with the accompanying drawings forming a part hereof, wherein reference numerals refer to like parts throughout the several views.

FIG. 9 is a side elevational view of the embodiment shown in FIG. 7.

FIG. 10 is a top plan view of the embodiment shown in FIG. 7.

FIG. 11 is a top plan view of the embodiment shown in FIG. 7, wherein the frangible portion has been removed, further showing the relationship between the gel and wicks when the gel is in use.

DESCRIPTION OF THE PREFERRED EMBODIMENTS

Figure 1:
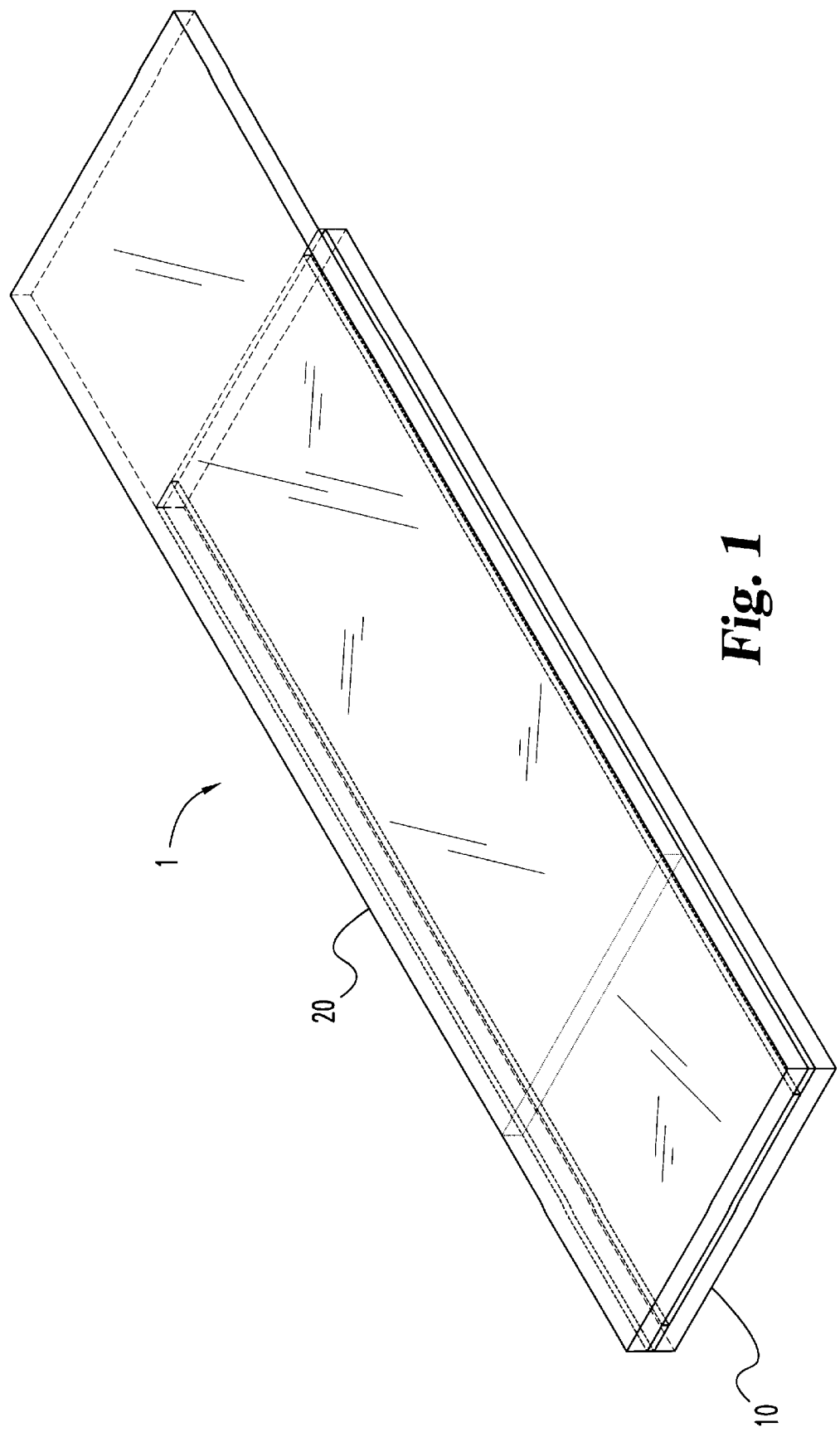
FIG. 1 is a perspective view of a preferred embodiment of an ultra-thin, miniature, disposable slab gel of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
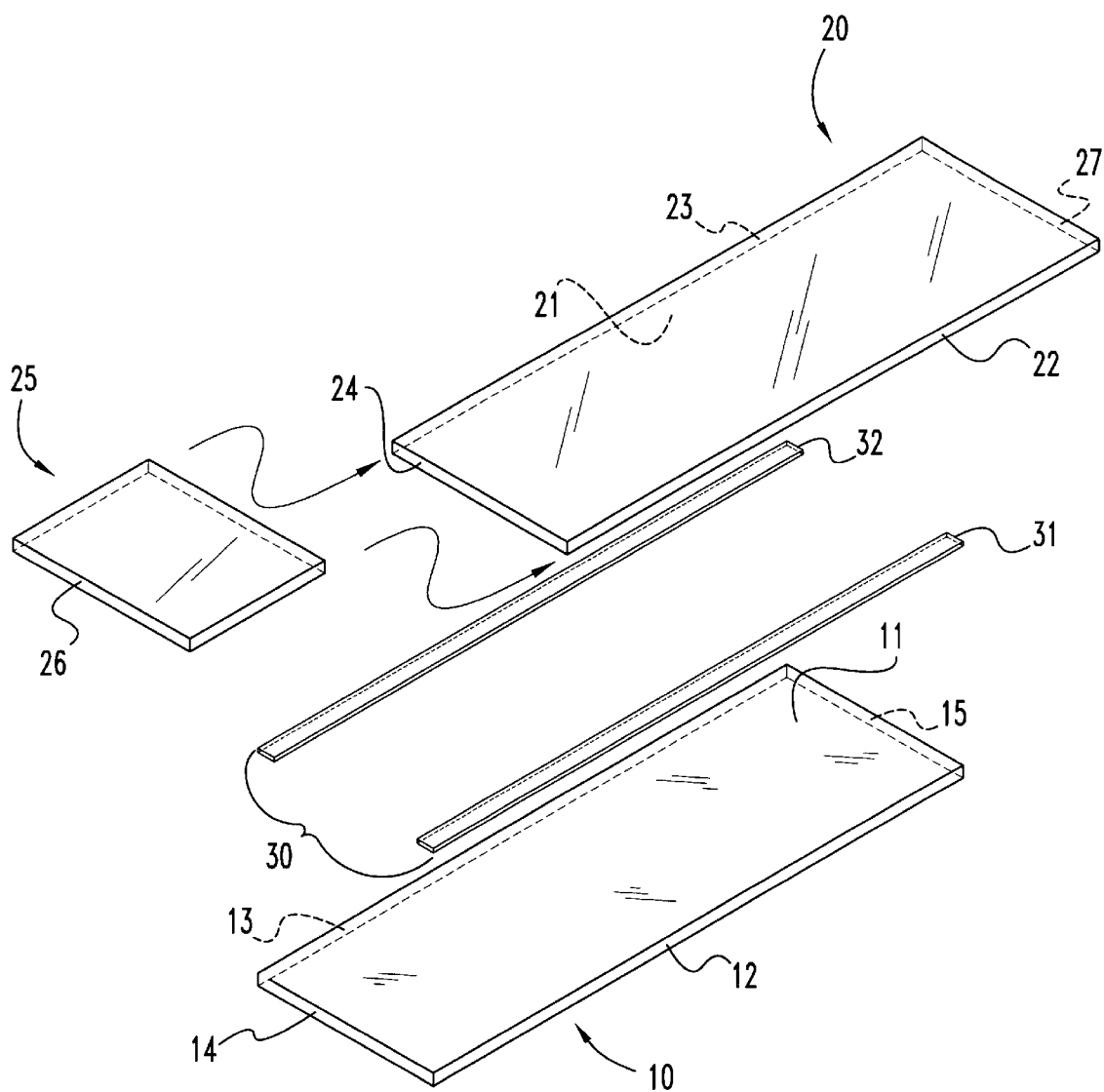
FIG. 2 is an exploded perspective view of the slab gel of FIG. 1.
Figure 3:
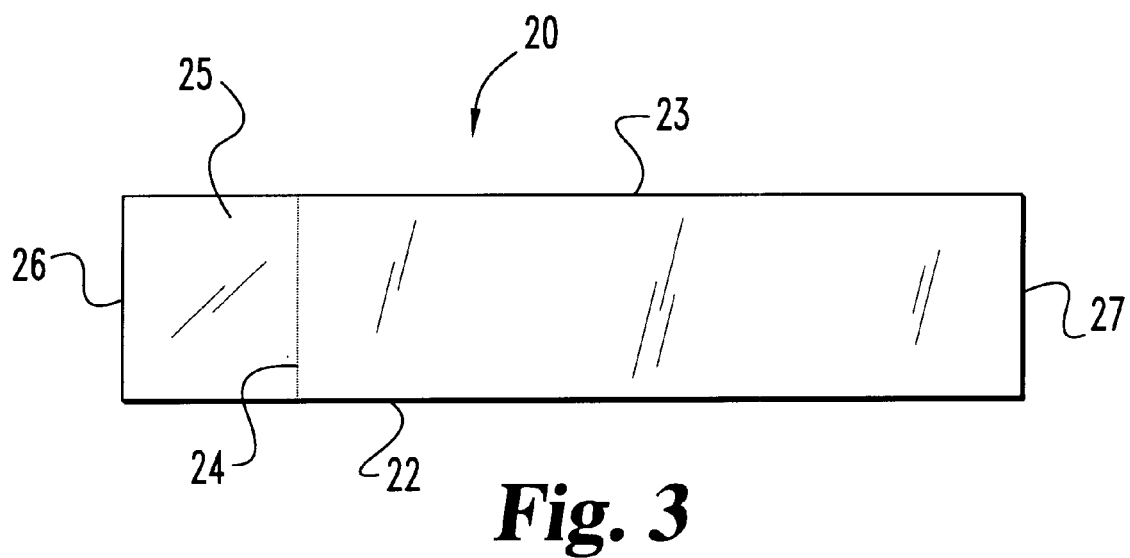
FIG. 3 is a top plan view of a top plate according to the embodiment shown in FIG. 1.
Figure 4:
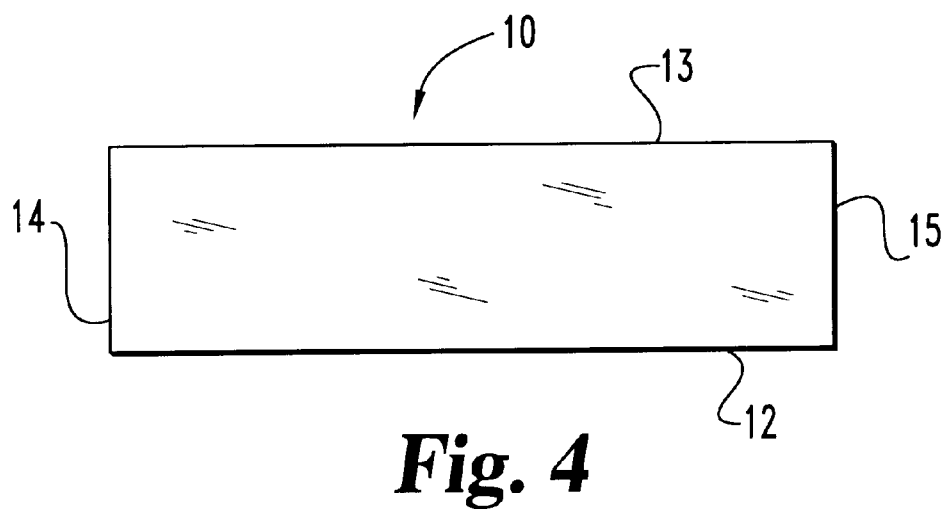
FIG. 4 is a top plan view of a bottom plate according to the embodiment shown in FIG. 1.
Figure 5:
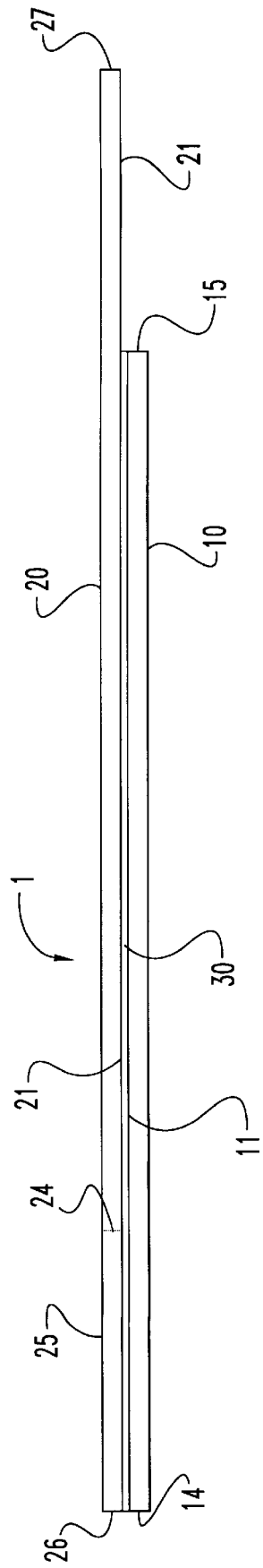
FIG. 5 is a side elevational view of the embodiment shown in FIG. 1.

For purposes of describing the present invention, reference will first be made to one preferred embodiment of an ultrathin, miniature, disposable slab gel 1, which is illustrated in FIG. 1. FIG. 2 shows the same embodiment in an exploded view. As is seen in FIG. 2, the gel 1 of this embodiment of the present invention comprises a bottom plate 10 having a first interior surface 11. Additionally, the bottom plate 10 has a first side margin 12, a second side margin 13, a first end 14 and a second end 15. As is shown in FIG. 2, the gel 1 of this embodiment also comprises a top plate 20 having a second interior surface 21, overlying said bottom plate 10 in opposing spaced apart relationship. The top plate 20 also has a first side margin 22, a second side margin 23, a first end 24 and a second end 27. In this preferred embodiment, the top plate 20 also comprises an extension 25 which is attached to the first end 24 providing an extended first end 26 of the top plate 20.

A gel according to the present invention, for example, the gel 1 depicted in FIGS. 1 and 2, also comprises a spacing device 30 positioned between the top plate 20 and the bottom plate 21. A gel medium substantially fills a space between the first interior surface 11, the second interior surface 21, and the spacing device 30. The gel medium is adapted to permit migration of polynucleotides (DNA or RNA molecules) upon application of an electric field across the gel medium. Examples of gel media contemplated for use in accordance with the present invention include, for example, polyacrylamide gel, agarose, cellulose and granulated gels. However, this list is not exhaustive and any other useful medium is also contemplated for use in the present invention. The first interior surface 11 faces the second interior surface 21 and the distance between the first interior surface 11 and the second interior 21 surface is substantially uniform and within a range of about 10 $\mu$m to about 50 $\mu$m. This distance defines the thickness of the gel medium. After electrophoresis using this embodiment, when the plates are separated for analysis, the gel medium can be seen to completely and uniformly cover the first interior surface of the bottom plate which was previously chemically treated to bond to the gel.

In a preferred embodiment of the present invention, the spacing device 30 comprises a first spacing structure 31 and a second spacing structure 32. In use, the first spacing structure 31 is positioned between the first side margin 12 of the bottom plate 10 and the first side margin 22 of the top plate 20; and the second spacing structure 32 is positioned between the second side margin 13 of the bottom plate 10 and the second side margin 23 of the top plate 20. In one preferred embodiment the first and second spacing structures comprise $\frac{1}{16}$ inch-wide tape strips. Preferably, the first and second spacing structures comprise the thinnest possible tape. In an alternate embodiment, the first and second spacing structures comprise strips of thin plastic wrap material such as, for example, SARAN WRAP, a 12.5 $\mu$m thick polyvinylidine chloride sheet. It can be seen by one of ordinary skill in the art that the first and second spacing structures can be made from any thin material which has a consistent thickness to provide a tight seal between the top plate 20 and the bottom plate 10. In a preferred embodiment, the material is a plastic material. Additionally, as is understood by a person of ordinary skill in the art, the first and second spacing structures should have consistent widths, thus providing a gel medium having a consistent width when the spacing structures are placed flush with the side margins as above described. As such, said first and second spacing structures define a first edge and a second edge of the gel medium, the first edge and second edge preferably being substantially parallel to one another.

In accordance with the present invention, the length of the gel medium in a preferred embodiment is substantially uniform and within a range of about 50 mm to about 200 mm. More preferably, the length of the gel medium is substantially uniform and within a range of about 75 mm to about 100 mm. As used herein, gel medium length is defined by a distance of gel medium which extends between the top plate and the bottom plate. Due to the low hydrostatic pressure of the ultra-thin gel structure (gel sandwich), surface tension forces are sufficient to prevent the gel solution from leaking out the ends during assembly (as described more fully below) when the structure is removed from the gel solution. At the end of the gel medium of, for example, the preferred embodiment shown in FIG. 1, where the top plate extends beyond the bottom plate, excess polymerized gel medium is likely to form. This excess gel medium is easily scraped off with, for example, a razor blade after the gel medium is completely polymerized, when the gel is "cleaned up" for storage. As can be readily seen by one of ordinary skill in the art, excess polymerized gel medium is likely to form at various locations on alternate embodiments where there is a point of overlap between the top plate and the bottom plate. Excess gel medium forming at such a location is easily removed as described.

In a preferred embodiment of the present invention, the bottom plate and the top plate comprise standard microscope slides. The term "standard microscope slide", as used herein is intended to designate a microscope slide having the following dimensions: 1 inch×3 inches (25 mm×75 mm; thickness of from about 0.93 mm to about 1.05 mm). It can be readily seen that alternative embodiments are made from microscope slides having the dimensions 1.5 inch×3 inches, 2 inches×3 inches or a wide variety of other dimensions capable of maintaining the integrity of the gel medium thickness. As used herein, the term "microscope slide" is intended to designate plates actually made to be used as microscope slides and a wide variety of other plates similar thereto.

According to the present invention, more samples could be analyzed simultaneously using a gel having wider plates;

however, making the gel significantly larger might require using expensive polished glass plates to ensure uniform flatness. Additionally, it can be seen that gels according to the present invention could be made wherein the top plate and/or the bottom plate comprise plastic or other equally useful material.

In one preferred embodiment, the bottom plate comprises a microscope slide which has a frosted area, this type of slide being well known in the art. The white frosting on the slide is useful to aid in the loading of the samples onto the gel medium. As can be readily seen, the frosted side of the slide is preferably on the side of the slide opposite the first interior surface and, as such, is not adjacent the gel medium.

The most preferred microscope slides used according to the present invention are standard, pre-cleaned, GOLD SEAL, Clay Adams, made of Swiss Glass, which may be obtained from Baxter Scientific Products, McGaw Park, Ill. A preferred frosted slide is catalogue no. 3050, and a preferred regular (unfrosted) slide is catalogue no. 3011.

In a preferred embodiment of the present invention, for example the embodiment depicted in FIG. 1, the top plate 20 comprises a standard microscope slide and an extension 25 removeably attached to the first end 24 of the microscope slide, resulting in an extended first end 26. The extension preferably is an approximately 0.5-inch-long segment of a standard microscope slide. To prepare a top plate 20 having a removeably attached extension 25, a 0.5-inch-long glass extension may be cut from one end of a standard microscope slide. The 0.5-inch-long piece of glass is preferably attached to a first end 24 of the top plate 20 by placing the manufacturer's edge of the extension 25 against the first end 24 of a whole standard microscope slide. Pressure is exerted lengthwise on the junction and care is taken to maintain an even contact between the whole slide and the extension. Then, a small amount of glue, for example, liquid cyanoacrylate glue, is preferably applied to the junction near the center of the plate. The glue is then spread toward the edges of the slide while pressure is maintained for a period of time sufficient to allow bonding (about 10 seconds). Care should be taken to ensure that no glue leaks through the junction to the opposite side of the plate. Such leaking causes glue to be deposited on the second interior surface 21 of the top plate 20, and indicates a leaky junction. Leaky junctions tend to trap bubbles, making holes in the gel medium and distorting separation of bands during DNA analysis. Thus, in a preferred embodiment, the portion of the gel medium adjacent the second interior surface 21 of the top plate 20 is smooth. As such, the removal of the extension 25 prior to use will expose a portion of the gel medium to be used as a loading region which has substantially no indentations and which is free from sample wells such as those required in conventional gels.

In the preferred embodiment shown in FIG. 1, the top plate 20 is oriented in relation to the bottom plate 10 such that the extended first end 26 is substantially flush with the first end 14 of the bottom plate 10. This orientation will allow the extension 25 to be removed, prior to use, exposing a portion of the gel medium beneath it. Alternatively, the extended first end 26 of the top plate may protrude slightly beyond the first end 14 of the bottom plate 10. This orientation may serve to facilitate removal of the extension 25 prior to or during use by simply exerting an upward force upon the extended first end 26 while ensuring that the top plate and bottom plate remain in tight contact with the spacing device.

As has been shown and described, in this preferred embodiment the top plate comprises a standard microscope slide and an extension 25, and thus is longer than the bottom plate 10 which comprises a standard microscope slide. As such, the second end 27 of the top plate 20 extends beyond the second end 15 of the bottom plate 10. This orientation is useful to facilitate contact between the exposed end of the gel medium 40 and an electrical source for polynucleotide separation.

In an alternate preferred embodiment, there is provided a gel which differs from the gel shown in FIG. 1 in that, instead of attaching a removeable extension to the first end of the top plate, the top plate is scored to provide a removeable frangible portion of the top plate. According to this alternate preferred embodiment of the present invention, shown in FIGS. 7–11, the top plate 120 has a score line 171 across the width of the top plate 120 on the second interior surface 121 of the top plate 120. The score line 171 is preferably substantially closer to a first end 124 of the top plate 120 than to a second end 127 of the top plate 120, thus providing a frangible portion 172 of the top plate 120 at the first end 124 of the top plate 120 that may be conveniently removed to expose a portion of the gel medium to be used as a loading region. As used herein, "frangible portion" is intended to designate the portion of the top plate 120 between the first end 124 of the top plate 120 and the score line. The score line 171 is more preferably located about 0.5 inches from the first end 124. To prepare a top plate having a score line 171, a hard material, for example tungsten carbide or diamond stylus is used to score the top plate 120 in a substantially straight line across its width. The score line 171 is placed on the second interior surface 121 so that the frangible portion 172 may be cleanly snapped off prior to using the gel upon application of an upward force on the first end 124 of the top plate, thus exposing a portion of the gel medium.

According to this preferred embodiment, the top plate 120 is oriented in relation to the bottom plate 110 such that the first end 124 of the top plate 120 protrudes beyond the first end 114 of the bottom plate 110 to provide an overhanging section 173 of the top plate 120. The score line 171 of this embodiment is preferably a distance from the overhanging section 173 and, thus, part of the frangible portion 172 overlies the bottom plate 110 and part of the frangible portion 172 protrudes beyond the first end 114 of the bottom plate 110. As such, removal of the frangible portion 172 during use exposes a portion of the gel medium to be used as a loading region.

As has been shown and described in accordance with this alternative preferred embodiment, where, for example, the top plate 120 and the bottom plate 110 are each standard microscope slides and the first end 124 of the top plate 120 protrudes beyond the first end 114 of the bottom plate 110, the second end 115 of the bottom plate 110 also protrudes beyond the second end 127 of the top plate 120, thus providing an exposed section of the bottom plate. This orientation is useful to facilitate contact between the exposed end of the gel medium and an electrical source for polynucleotide separation.

Figure 12:
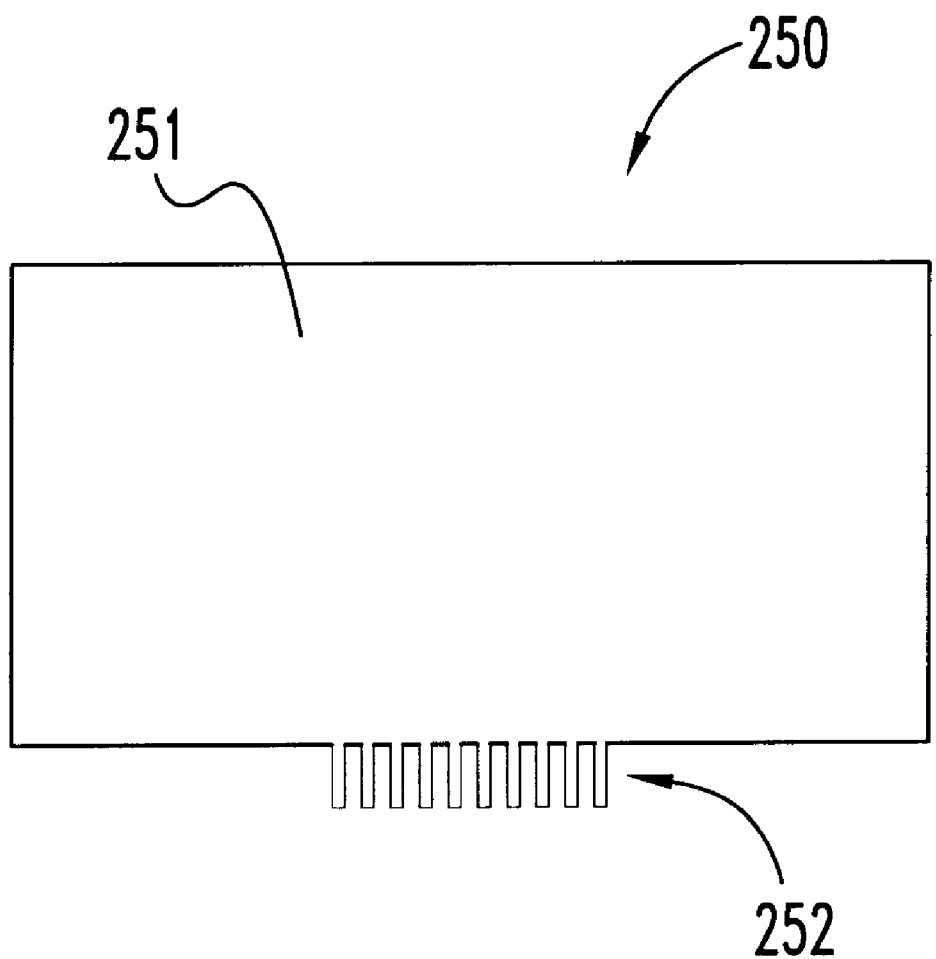
FIG. 12 is a side elevational view of a sample transferring device according to the present invention.
Figure 13A:
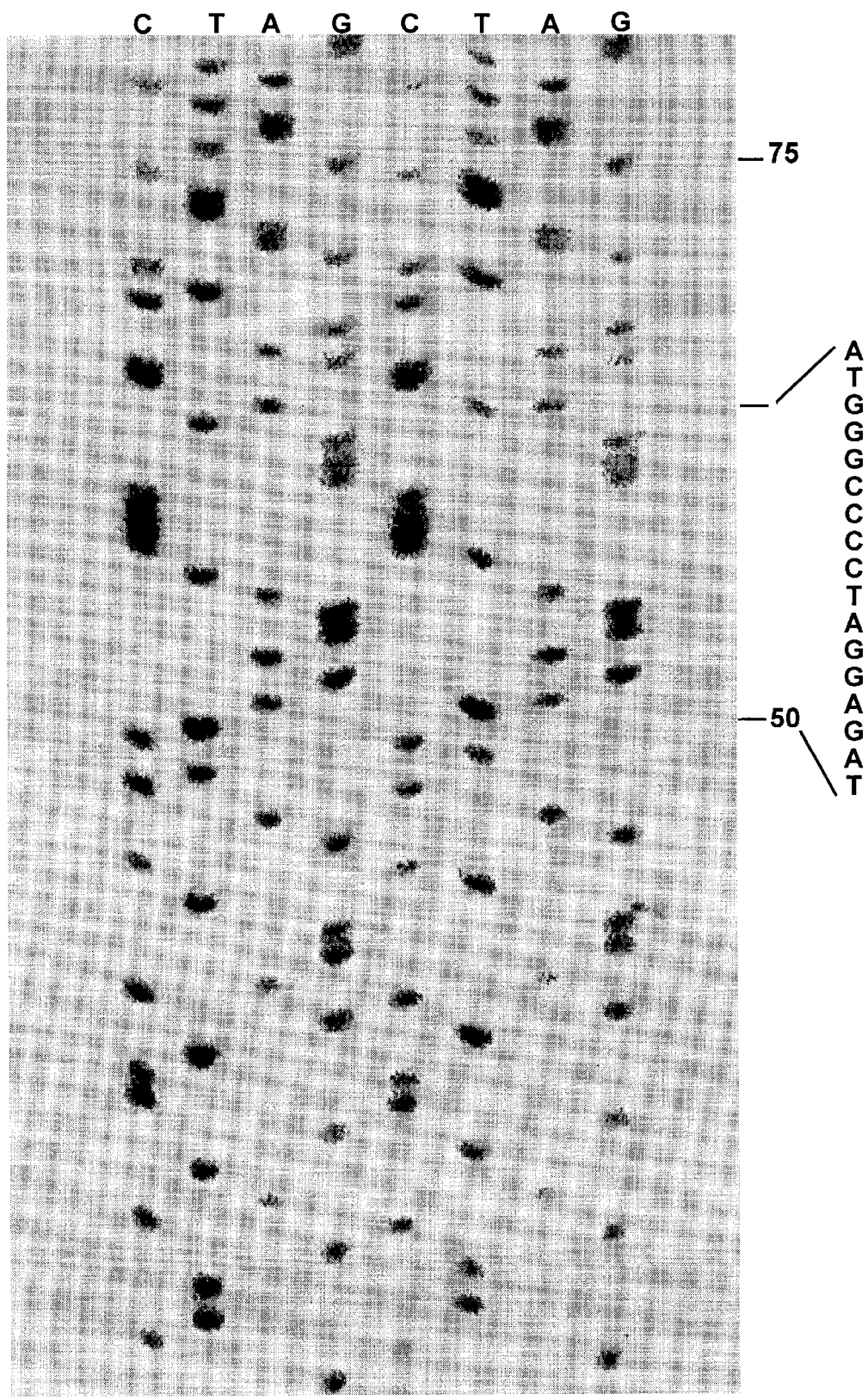
FIG. 13 is a computer print-out of an 8-times enlarged digital image, obtained by scanning a miniaturized gel membrane after colorimetric detection as described in the specification. The sheet marked "13A" includes the lower half of the gel and the sheet marked "13B" includes the upper half of the same gel. Two loadings of the same sequencing reactions terminated at C, T, A or G are shown. Nucleotide chain numbers extending from the end of the primer are indicated. The known DNA sequence corresponding to a region of the ladders is indicated.
Figure 13B:
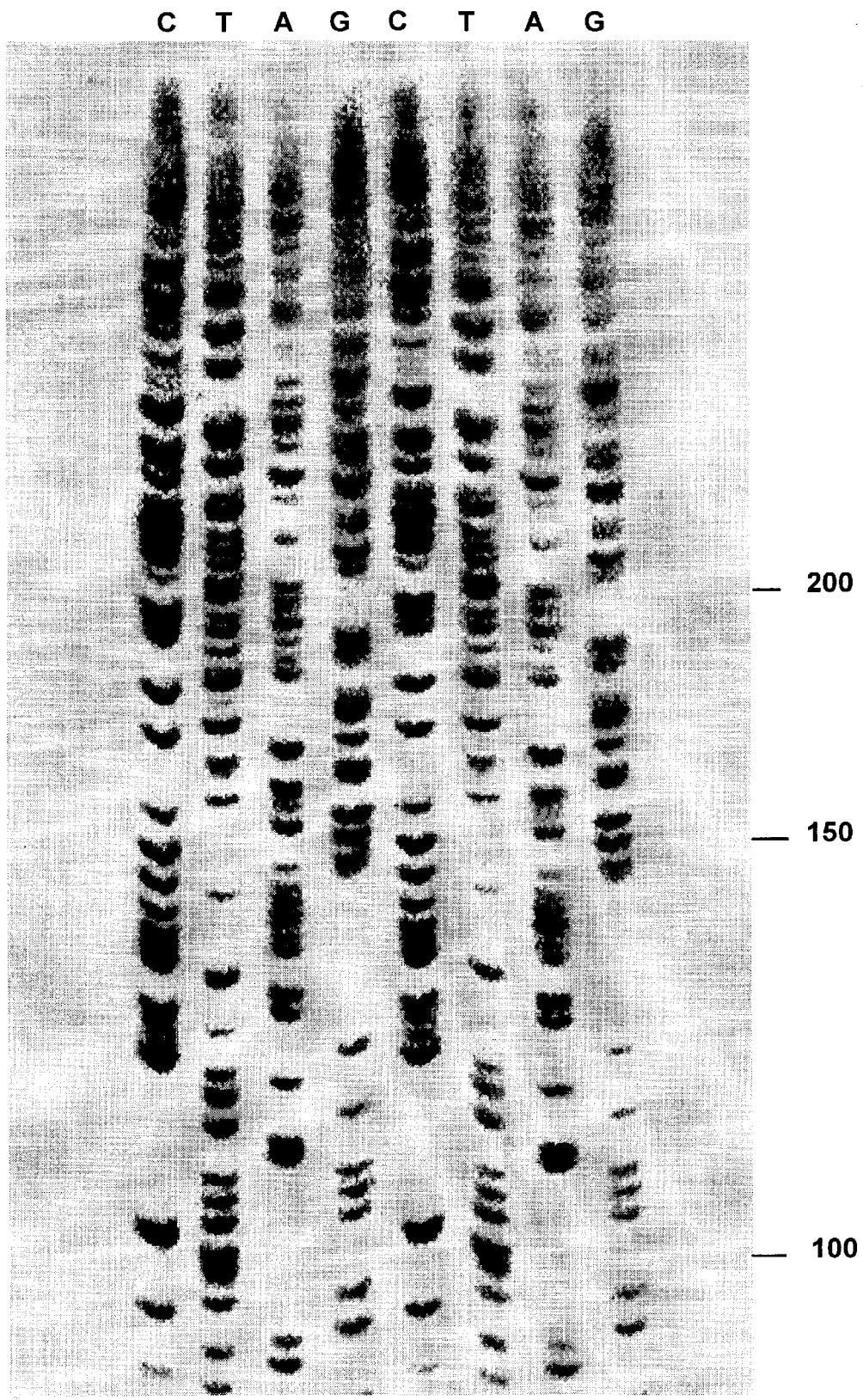

Also in accordance with the present invention, FIG. 12 illustrates a preferred embodiment of a device 250 for transferring samples to a gel for electrophoresis. As is seen in FIG. 12, the transferring device 250 of the present invention comprises a body 251 having a predetermined number of teeth 252 extending therefrom. Each tooth of the transferring device defines a corresponding longitudinal axis. Each tooth has a proximal end defined as the end of the tooth connected to the body, and a distal end defined as the end of the tooth furthest from the body. The distance between the proximal end and the distal end of each tooth is preferably within a range of about 1.0 mm to about 2.5 mm. The longitudinal axes preferably are substantially parallel to each other and lie substantially in a plane. In a preferred embodiment, the distal ends of all of the teeth substantially lie in a line which is substantially perpendicular to a longitudinal axis of any of the teeth. The teeth are preferably from about 0.010 inches to about 0.025 inches wide and from about 0.005 inches to about 0.010 inches thick; the teeth are preferably closely spaced, and in a preferred embodiment the thickness of the distal end of each tooth is reduced to a sharp edge.

A preferred embodiment of a device 250 for transferring samples to a gel system for electrophoresis may be fashioned from a single edged, no. 9 razor blade (VRW) by spark erosion, using a brass template electrode and an electric discharge machine. In this embodiment, the bottom of each tooth maintains the sharp razor blade edge. It can readily be seen by one of ordinary skill in the art, that a transferring device 250 according to the present invention can be made of alternate materials and by alternate procedures. It is intended that the present invention encompass all such transferring devices 250 having substantially razor sharp teeth to be useful for loading samples onto gels for electrophoresis in accordance with the present invention.

Also, according to the present invention, there is provided a method for preparing inventive ultra-thin, miniature, disposable slab gels. This method comprises providing a sequencing gel solution in which polymerization is initiated; causing a bottom plate, a top plate and a spacing device to be substantially submerged in the solution; and making a gel sandwich while the plates and the spacing device are substantially submerged in the solution. The phrase "making a gel sandwich," as used herein, is meant to refer to assembling the gel of the present invention by placing the top plate and the bottom plate in opposing spaced apart relationship with one another, with the spacing device oriented therebetween as is shown, for example, in FIG. 1 or, alternatively, in FIG. 7. The gel sandwich is then removed from the solution and, in a preferred embodiment, a substantially even inward pressure on the bottom plate and the top plate is provided for a period of time. "Substantially even inward pressure", as used herein, is intended to designate a pressure which does not vary by more than about 20%, and which presses the top plate toward the bottom plate, thereby providing a tight seal between the top plate, the spacing device and the bottom plate. The inward pressure is preferably continued for a period of time which ends after the gel solution is completely polymerized into a gel medium. In a preferred method, the spacing structures are affixed to one or both of the bottom plate and the top plate prior to submerging the bottom plate, the top plate and the spacing structures in the gel solution. Most preferably, the spacing structures are affixed to the bottom plate prior to submersion in the gel solution.

One of the most significant teachings of the present invention is a method for loading samples onto a gel which causes only minor disruption to the surface of the gel medium. This method comprises providing a gel wherein the loading region of the gel medium is exposed; providing a transferring device according to the teachings of the present invention for transferring samples to a gel; wetting one or more of the teeth of the transferring device with an effective amount of one or more samples; and stamping the teeth of the transferring device into the loading region of the gel medium such that the teeth cut substantially through the gel medium. This method is advantageous in light of methods for loading samples in the prior art, for example, because it obviates the need for providing sample wells in the gel medium and it applies the samples as razor-sharp bands. This advantageously leads to DNA separation having a very high resolution.

In a preferred embodiment, the wetting step comprises loading 100 to 200 nanoliters of sample on each tooth using a standard sub-microliter pipetting device. Excess sample (typically about half of the volume) may be blotted off so the gel will not be overloaded. In an alternate method of wetting the teeth of the transferring device, a sample well apparatus may be provided having one or more sample wells which correspond to one or more of the teeth. More preferably, impressions of the teeth can be made in three layers of pressed laboratory PARAFILM, the impressions thus serving as sample wells. The sample well spacing then precisely matches the spacing of the teeth. Using this method, about 50–100 nanoliters of sample is pipetted into each well to be loaded. The samples are then easily scooped out of the wells by a swipe of the transferring device, and the teeth pick up optimal amounts of samples for loading.

In a preferred embodiment, the samples are stamped into the gel medium using the razor-sharp teeth of the transferring device while the electrical source is turned off. The razor-sharp teeth cut through the gel medium creating wells and, at the same time, the wells become loaded with samples. This method advantageously gives sharp bands, and is important in order to achieve high resolution.

As can be seen by one of ordinary skill in the art, the present invention additionally teaches a method for performing high resolution DNA analysis comprising loading one or more samples onto a gel according to the loading method above described; applying a predetermined electric field for a length of time effective to separate components of the sample in the gel medium; and detecting the separated sample components. The detection step can be accomplished using any conventional method of detection. As can be seen by one of ordinary skill in the art, there are many gel detection methods including fluorsecence, radioactive detection, colorimetric detection, and others. A wide variety of detection techniques are advantageously used in accordance with the present invention.

The invention will be further described with reference to the following specific Examples. It will be understood that these Examples are illustrative and not restrictive in nature.

EXAMPLE ONE

Making a Gel Having a Top Plate which Comprises an Extended First End

Microscope slides were selected for use as a bottom plate and a top plate. The slide to be used as a bottom plate was a frosted microscope slide and the side of the slide opposite the frosting was treated with γ-methacryloxypropyltrimethoxy-silane, as described for glass surfaces (Garoff, H. Ansorge, W., Analyt. Biochem 115, 450–57, 1981), to bond the polyacrylamide to the glass. Tape strips $\frac{1}{16}$ in. wide were placed along each side margin of this slide. The unfrosted and untreated microscope slide to be used as the top plate was affixed with an extension as described above to provide a smooth, leak-free extended top plate.

A standard recipe sequencing gel solution (60 ml) was prepared consisting of 4.0–8.0% acrylamide (19:1 acrylamide to bisacrylamide ratio), 8.3 M urea, and Tris Borate-EDTA (TBE) buffer. The solution was filtered and degassed, as usual. Ammonium persulfate and TEMED were added to initiate polymerization, and the solution was poured into a 150 mm×25 mm polystyrene cell culture dish. The amount of TEMED used was an amount such that polymerization occurred in about 30 minutes. Next the top plate and the bottom plate, to which the spacing device was already attached, were submerged in the gel solution and placed together to make a gel sandwich such that the first interior surface faced the second interior surface, the first end of the bottom plate was flush with the extended first end of the top plate, the first side margin of the bottom plate was flush with the first side margin of the top plate and the second side margin of the bottom plate was flush with the second side margin of the top plate.

Then the gel sandwich was withdrawn from the solution and a weight was placed upon the gel sandwich to apply a substantially even pressure during polymerization, resulting in a uniform ultra-thin gel medium. To facilitate withdrawal, a dish was used which had a microscope slide glued to the bottom as a platform from which the gel sandwiches could be more easily grasped. Two stacked 2×4×¼ in., 74 g glass plates per gel were used as weights. Usually, 10 gels were made at one time, using the same gel solution. The polymerizing gels were left undisturbed for one hour, and then the gel sandwiches were cleaned by scraping off any excess polyacrylamide formed on the outside of the plates and by rinsing off crystallized urea. The gels were inspected to see if any bubbles were present and were then stored in a TBE-Urea solution in a closed container for later use.

EXAMPLE TWO

Making a Gel Having a Top Plate which Comprises a Score Line

Microscope slides were selected for use as a bottom plate and a top plate. The slide to be used as a bottom plate was a frosted microscope slide and the side of the slide opposite the frosting was treated with γ-methacryloxypropyltrimethoxy-silane, as described for glass surfaces (Garoff, H. Ansorge, W., Analyt. Biochem 115, 450–57, 1981), to bond the polyacrylamide to the glass. Tape strips ¹⁄₁₆ in. wide were placed along each side margin of this slide. The unfrosted and untreated microscope slide to be used as the top plate was scored across the width of the slide approximately 0.5 inches from a first end of the slide using a diamond stylus as described above to provide a top plate having a frangible portion which may be readily snapped off. The score line was placed upon the surface of the slide which would become the first interior surface when the gel sandwich was assembled.

A standard recipe sequencing gel solution (60 ml) was prepared consisting of 4.0–8.0% acrylamide (19:1 acrylamide to bisacrylamide ratio), 8.3 M urea, and Tris Borate-EDTA (TBE) buffer. The solution was filtered and degassed, as usual. Ammonium persulfate and TEMED were added to initiate polymerization, and the solution was poured into a 150 mm×25 mm polystyrene cell culture dish. The amount of TEMED used was an amount such that polymerization occurred in about 30 minutes. Next the top plate and the bottom plate, to which the spacing device was already attached, were submerged in the gel solution and placed together to make a gel sandwich such that the first interior surface faced the second interior surface, the first end of the top plate extended beyond the first end of the bottom plate such that only a part of the frangible portion extended beyond the first end of the bottom plate and the score line was on a portion of the first interior surface overlying the bottom plate. Additionally, the first side margin of the bottom plate was flush with the first side margin of the top plate and the second side margin of the bottom plate was flush with the second side margin of the top plate.

Then the gel sandwich was withdrawn from the solution and a weight was placed upon the gel sandwich to apply a substantially even pressure during polymerization, resulting in a uniform ultra-thin gel medium. To facilitate withdrawal, a dish was used which had a microscope slide glued to the bottom as a platform from which the gel sandwiches could be more easily grasped. Two stacked 2×4×¼ in., 74 g glass plates per gel were used as weights. Usually, 10 gels were made at one time, using the same gel solution. The polymerizing gels were left undisturbed for one hour, and then the gel sandwiches were cleaned by scraping off any excess polyacrylamide formed on the outside of the plates and by rinsing off crystallized urea. The gels were inspected to see if any bubbles were present and were then stored in a TBE-Urea solution in a closed container for later use.

EXAMPLE THREE

Loading and Running the Gel

Figure 6:
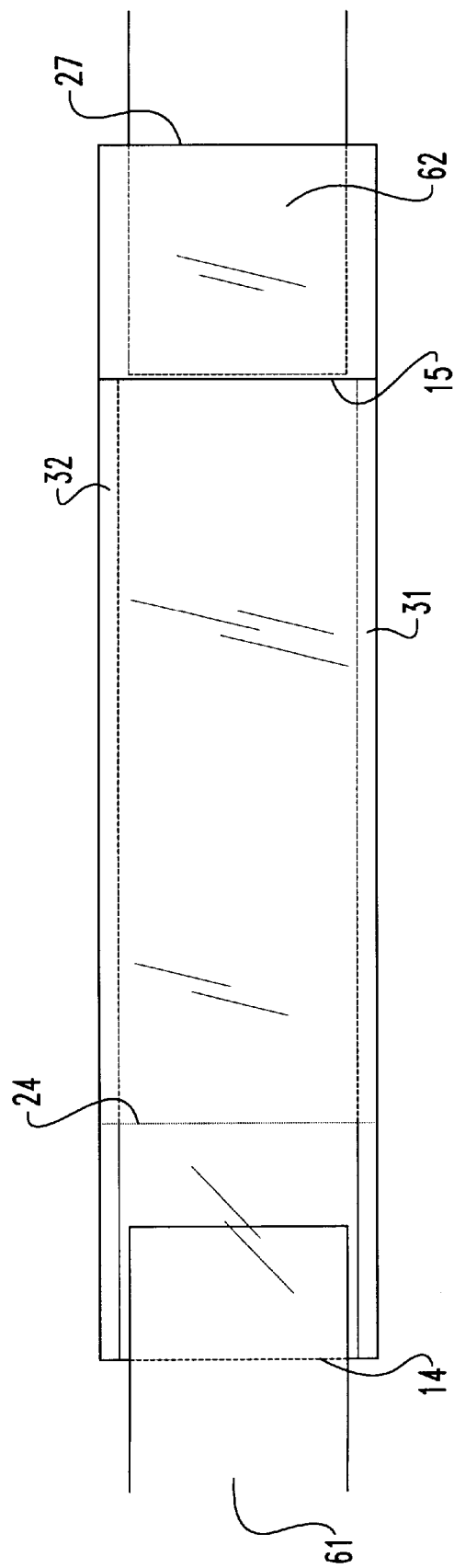
FIG. 6 is a top plan view of the embodiment shown in FIG. 1, wherein the extension has been removed, further showing the relationship between the gel and wicks when the gel is in use.
Figure 7:
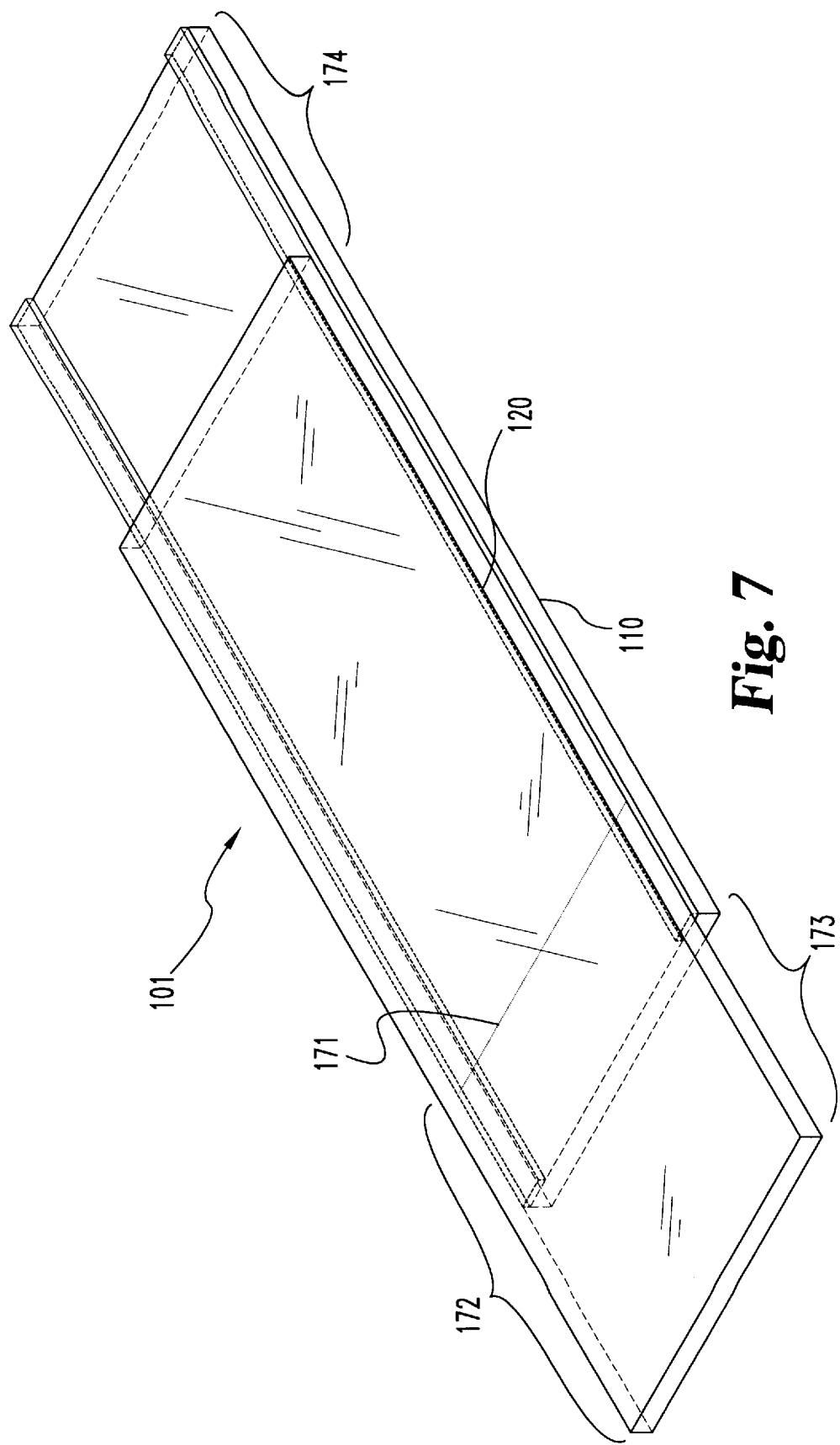
FIG. 7 is a perspective view of an alternate preferred embodiment of an inventive ultra-thin, miniature, disposable slab gel.

A gel, made according to either Example 1 or Example 2, was prepared for running by exposing a loading region for sample loading. For a gel made according to Example 1, this was accomplished by snapping off the extension using a razor blade; for a gel made according to Example 2, this was accomplished by snapping off the frangible portion. Two 2 cm×5 cm wicks were wetted in gel storage buffer and placed in contact with the gel medium ends. For a gel made according to Example 1, illustrated in FIG. 6, the second wick 62 was placed under the overhanging top plate, while the first wick 61 was placed on top of the exposed gel medium. For a gel made in accordance with Example 2, the second wick 162 was placed on top of the protruding second end of the bottom plate, and the first wick 161 was placed on top of the exposed medium. Whatman 3 MM Chromatography Paper was used for wicks. The gel system with wicks in place was then placed into an ordinary horizontal mini-agarose gel apparatus (BRL Model H6). Buffer was added to each compartment to a level several centimeters below the gel medium, making contact with the wicks, and the gel medium was pre-run for 30 seconds. At 900 V, a current of 2 to 3 milliamps is usually obtained which heats the gel medium to only about 40° C. over a course of about a 7 minute run.

Before loading, samples were heated 5 minutes at 80° C.–100° C., and placed on ice as usual. Then 50 to 100 nanoliters of each sample were deposited onto each tooth of the transferring device. This was done by loading 100 to 200 nanoliters of sample on each tooth using a standard microliter pipetting device. The teeth, wetted with samples, were then stamped into the gel medium in the loading region. Sufficient pressure was used so that the teeth cut completely through the gel medium. Using a smooth upward motion of the transferring device, the teeth were withdrawn from the gel medium, leaving separate razor-sharp bands of loaded samples. The power supply was then switched on (900 V), and electrophoresis began. The power was turned off briefly at 2.5 minutes to adjust the left wick to cover the loading region and electrophoresis was then resumed. At 900 V, the bromophenol blue dye marker was seen to enter the right-hand wick after about 6 minutes.

EXAMPLE FOUR

Post-Electrophoretic Gel Medium Analysis

At the end of the run the top plate was removed, for example by using a razor blade, and discarded. The spacing structures were then removed, and the gel medium, supported by the bottom plate was fixed and dried for autoradiography. The gel medium, supported by the bottom plate, was soaked in a 10% methanol, 10% acetic acid mixture for 5 minutes. The gel medium was then dried by placing the bottom plate, still supporting the gel medium, on a heating block at 70° C. for 5 minutes, resulting in a very thin, hard, transparent gel film on the glass. The dried gel film was then exposed to x-ray film or used in a phosphoimager.

Alternatively, the gel medium can be blotted and processed for colorimetric detection. In this type of analysis, a biotinylated sequencing primer is used in the sequencing reactions. The gel is run as before, then immediately blotted by placing the gel medium in direct contact with a piece of wet nylon hybridization membrane, upon which a piece of dry filter paper and a weight are placed. After 10–15 minutes the DNA bands become nearly quantitatively transferred to the membrane, as they were on the gel, and the DNA is then fixed to the membrane by UV crosslinking, a standard procedure used with blotting, requiring less then 2 minutes. Next, the membrane is washed and treated with commercially available reagents and this results in attachment of alkaline phosphatase to the DNA, a procedure that takes about 45 minutes. Finally, the membrane is submerged in a solution containing the commercially available colorimetric reagent, NBT/BCIP for about 2 hours, rinsed briefly with water, and dried with a hair dryer. Bands appear blue on a white background, and remain visible for several months.

Figure 8:
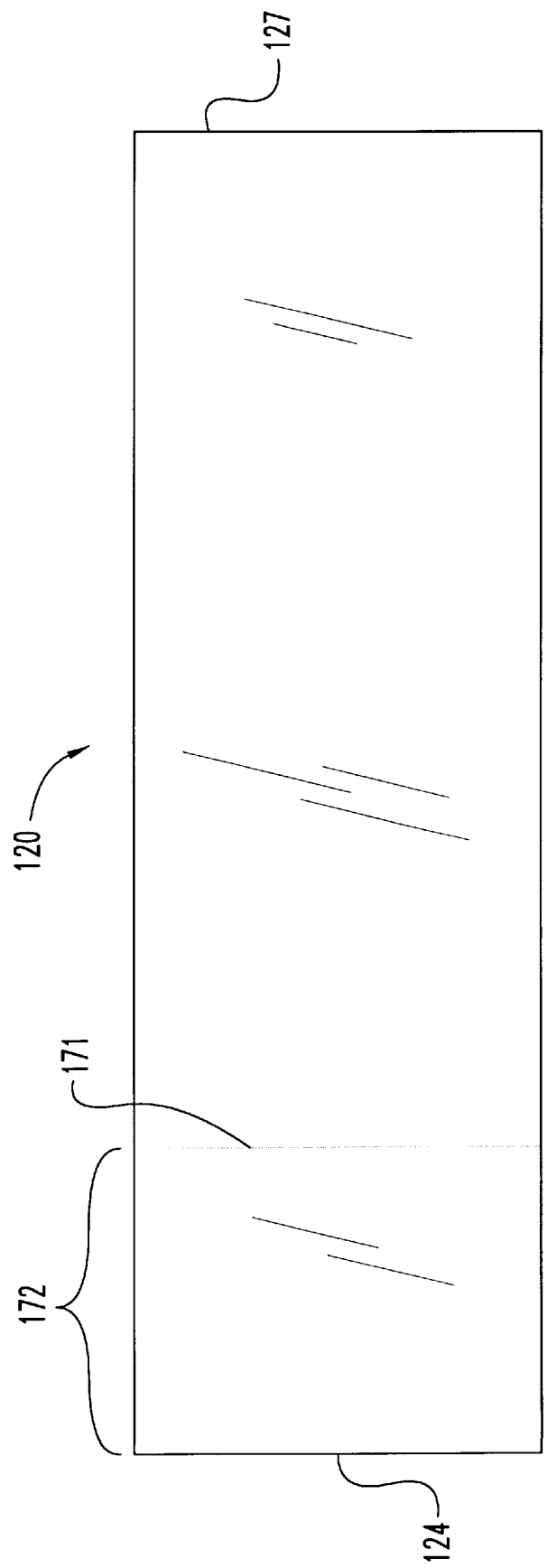
FIG. 8 is a top plan view of a top plate according to the embodiment shown in FIG. 7.

The image on the membrane, processed as described above, may then be scanned using a high resolution scanner, converting it to a digital form, which may be stored indefinately on a floppy disk. The image may be enlarged and viewed on a computer terminal screen using a variety of software, and it may be printed using an ordinary laser printer. An 8-fold enlarged image thus produced is shown in FIG. 8. The bands are almost as sharp as those obtained using the isotpe S-35, as described above, and the DNA sequence is readable by eye from this image for about 150 nucleotides from the primer.

There are advantages of colorimetric detection over isotope detection. First, the time required by the colorimetric method is significantly shorter. Using S-35 isotope, film exposure of 16 hours or more are generally required, whereas results can be obtained in only 2–3 hours using the colorimetric method described above. Second, the colorimetric reagents are stable over long periods of time, and do not pose a radiological hazard. These properties make this method ideal for student instruction.

Reagents have been available for several years for colorimetric detection of DNA blotted from sequencing gels. However, this method has not been widely used because of the costs of the reagents and the inconvenience of working with large gels and membranes. For example, the amount of nylon hybridization membrane required to blot one standard size sequencing gel costs between about $30.00 and $40.00, and the required chemical reagents to process the membrane in large trays cost between about $15.00 and $25.00. Thus, one gel could cost between about $45.00 and $65.00. In contrast, processing a gel of the present invention is easily done, and costs about $2.00 for the same supplies and reagents.

While the invention is described in connection with preferred embodiments, it will be understood that it is not intended to limit the invention to such embodiments. On the contrary, the invention is intended to cover all alternatives, modifications and equivalents as may be included within the spirit and scope of the invention as defined by the claims.

What is claimed is:

1. A method for loading one or more samples onto a gel medium comprising:

providing a gel comprising a bottom plate, a top plate overlying said bottom plate in opposing spaced apart relationship, a spacing device positioned between the top plate and the bottom plate and substantially uniformly spacing the top plate and the bottom plate, and a gel medium received within the space between the top plate and the bottom plate, wherein a loading region of the gel medium is exposed, and wherein the gel medium has a thickness of from about 10 $\mu$m to about 50 $\mu$m;

providing a device for transferring samples to the gel, comprising a body and a plurality of teeth extending from the body;

wetting one or more of the teeth with an amount of one or more of the samples;

stamping the teeth of the transferring device into the loading region of the gel medium such that the teeth cut substantially through the gel medium; and withdrawing the teeth from the gel medium without substantially disrupting the surface of the gel medium, thereby forming one or more sharp bands of sample in the gel medium.

2. The method of claim 1 in which the loading region of the gel medium is substantially free from indentations.

3. The method of claim 1 in which said wetting step comprises the steps of:

providing a number of samples in a sample well apparatus including a plurality of wells; and inserting the transferring device into the sample well apparatus such that each of the teeth enters a corresponding well.

4. The method of claim 1 in which said wetting step comprises the steps of:

pipetting from about 100 to about 200 nanoliters of sample onto one or more teeth; and blotting off excess sample.

5. A method for performing high resolution DNA analysis comprising:

providing a gel comprising a top plate, a bottom plate, a spacing device positioned between the top plate and the bottom plate, and a gel medium received within the space between the top plate and the bottom plate, wherein a portion of the gel medium is exposed, and wherein the gel medium has a thickness of from about 10 $\mu$m to about 50 $\mu$m; and a device for transferring DNA samples to the gel which comprises a body and a plurality of teeth extending from the body;

loading one or more samples onto the gel medium by wetting one or more of the teeth with one or more of the DNA samples; stamping the teeth into the loading region such that the teeth cut substantially through the gel medium; and withdrawing the teeth from the gel medium without substantially disrupting the surface of the gel medium, thereby forming a first set of one or more sharp bands of sample in the gel medium;

applying a predetermined electric field to the gel medium for a length of time effective to separate components of the sample into a second set of bands on the gel medium; and detecting the second set of bands on the gel medium.

6. A method for performing high resolution DNA analysis comprising:

providing a gel comprising a top plate, a bottom plate, a spacing device positioned between the top plate and the bottom plate, and a gel medium received within the space between the top plate and the bottom plate, wherein a portion of the gel medium is exposed, and wherein the gel medium has a thickness of from about 10 μm to about 50 μm; and a device for transferring DNA samples to the gel which comprises a body and a plurality of teeth extending from the body;

loading one or more samples onto the gel medium by wetting one or more of the teeth with one or more of the DNA samples and stamping the teeth into the loading region such that the teeth cut substantially through the gel medium; and withdrawing the teeth from the gel medium, thereby forming a first set of one or more sharp bands of sample in the gel medium, each band comprising less than about 200 nanoliters of sample;

applying a predetermined electric field to the gel medium for a length of time effective to separate components of the sample into a second set of bands on the gel medium; and detecting the second set of bands on the gel medium.

7. The method in accordance with claim 6, wherein the length of time is from about 6 to about 7 minutes.

\* \* \* \* \*